(12) United States Patent
Delmas et al.

(10) Patent No.: US 11,684,689 B2
(45) Date of Patent: Jun. 27, 2023

(54) SOLID POLYMERIC MATERIAL IMPREGNATED WITH A VOLATILE ORGANIC SUBSTANCE AND A SPECIFIC ESTER AND USES OF SAME

(71) Applicant: JAFER ENTERPRISES R&D SL, Granollers (ES)

(72) Inventors: Thomas Delmas, Saint Laurent du Var (FR); Marion Perez, Le Cannet (FR); Marine Le Bras, Sainte Lucie de Porto-Vecchio (FR); Antoine Gouteyron, Le Cannet (FR)

(73) Assignee: JAFER ENTERPRISES R&D SL, Granollers (ES)

( * ) Notice: Subject to any disclaimer, the term of this patent is extended or adjusted under 35 U.S.C. 154(b) by 226 days.

(21) Appl. No.: 16/960,950

(22) PCT Filed: Jan. 8, 2019

(86) PCT No.: PCT/EP2019/050303
§ 371 (c)(1),
(2) Date: Jul. 9, 2020

(87) PCT Pub. No.: WO2019/137894
PCT Pub. Date: Jul. 18, 2019

(65) Prior Publication Data
US 2020/0338225 A1 Oct. 29, 2020

(30) Foreign Application Priority Data

Jan. 11, 2018 (FR) ...................................... 1850218

(51) Int. Cl.
| | |
|---|---|
| *A61L 9/04* | (2006.01) |
| *C08J 7/02* | (2006.01) |
| *C11D 3/00* | (2006.01) |
| *C11D 3/37* | (2006.01) |
| *A61L 101/46* | (2006.01) |
| *A61Q 13/00* | (2006.01) |

(52) U.S. Cl.
CPC ................ *A61L 9/04* (2013.01); *A61L 9/042* (2013.01); *C08J 7/02* (2013.01); *C11D 3/0068* (2013.01);
(Continued)

(58) Field of Classification Search
None
See application file for complete search history.

(56) References Cited

U.S. PATENT DOCUMENTS

| | | | |
|---|---|---|---|
| 9,132,204 B2 * | 9/2015 | McKay | .................. A61L 9/013 |
| 2015/0020915 A1 | 1/2015 | Menon et al. | |

(Continued)

FOREIGN PATENT DOCUMENTS

| | | |
|---|---|---|
| WO | WO 02/47735 | 6/2002 |
| WO | WO 2016/138186 | 9/2016 |

(Continued)

OTHER PUBLICATIONS

English Machine Translation WO0247735 (A1) obtained Apr. 20, 2022 https://worldwide.espacenet.com/publicationDetails/biblio?CC=WO&NR=0247735A1&KC=A1&FT=D&ND=3&date=20020620&DB=EPODOC&locale=en_EP# (Year: 2002).*

(Continued)

*Primary Examiner* — Arrie L Reuther
(74) *Attorney, Agent, or Firm* — Saliwanchik, Lloyd & Eisenschenk

(57) ABSTRACT

The present invention concerns a solid polymeric material impregnated with a volatile organic substance (such as a perfume, an odour-masking agent or an insecticide) and a solvent comprising a $C_{10}$-$C_{18}$ monoester of $C_1$-$C_8$ alkyl that helps improve the rate of infusion of the volatile organic substance in the material and the diffusion profile of same. It also concerns a method for producing this material, and the uses of same for perfuming or deodorising the atmo- (Continued)

sphere, the body or laundry or as an insect repellent or insecticide. The invention also concerns a perfuming or deodorising product, an insect repellent or an insecticide comprising the above-mentioned material.

16 Claims, 3 Drawing Sheets

(52) U.S. Cl.
CPC ........... *C11D 3/373* (2013.01); *A61L 2101/46* (2020.08); *A61Q 13/00* (2013.01); *C08J 2383/04* (2013.01)

(56) References Cited

U.S. PATENT DOCUMENTS

2015/0030744 A1    1/2015   Lombardo et al.
2016/0354304 A1   12/2016   Anderson

FOREIGN PATENT DOCUMENTS

WO    WO 2018/122209    7/2018
WO    WO 2018/167206    9/2018

OTHER PUBLICATIONS

Written Opinion in International Application No. PCT/EP2019/050303, dated Feb. 13, 2019, pp. 1-4.
Singh, T. P. et al. "Phytochemical and pharmacological profile of *Zanthoxylum armatum* DC. -An overview" *Indian Journal of Natural Products and Resources*, Sep. 2011, pp. 275-285, vol. 2, No. 3.
Written Opinion in International Application No. PCT/EP2018/056519, dated May 9, 2018, pp. 1-6.
Pending claims in U.S. Appl. No. 16/494,427, filed Sep. 16, 2019, pp. 1-3.

* cited by examiner

SOLID POLYMERIC MATERIAL IMPREGNATED WITH A VOLATILE ORGANIC SUBSTANCE AND A SPECIFIC ESTER AND USES OF SAME

CROSS-REFERENCE TO RELATED APPLICATION

This application is the U.S. national stage application of International Patent Application No. PCT/EP2019/050303, filed Jan. 8, 2019.

FIELD OF THE INVENTION

The present invention relates to the field of articles used for fragrancing or deodorizing the atmosphere or laundry or as insect repellants or insecticides, which comprise a solid polymeric material impregnated with a volatile organic substance.

BACKGROUND OF THE INVENTION

The articles that are commercially available as solid diffusers of fragrances or of insecticides can take various forms suitable for their use. Mention will for example be made of anti-mosquito bracelets or diffusers in the form of pebble stones to be placed or to be suspended in order to fragrance laundry or cars. These products generally consist of an organic (particularly polymeric) matrix or an inorganic matrix (such as clay) into which the fragrance or the insecticide has been introduced by impregnation or sometimes, for polymer matrices, before polymerization of said matrix.

The drawback of these products is that the volatile substance that they contain has a tendency to evaporate rapidly at the start and is then released in insufficient amount, which is detrimental to the effectiveness of these diffusers over time.

In order to overcome this drawback, it has been proposed to combine the volatile substance with a diffusion regulator. Patent FR 1 601 586 thus describes cellular materials, preferentially based on cellulose, that are impregnated with volatile substances, more particularly with an insecticide, in which the rate of diffusion of the insecticide is regulated by addition of a compound making it possible to lower its vapor pressure, chosen in particular from certain alkyl diesters. These compounds are preferably combined with silicone oils which contribute to the controlled vaporization of the insecticide. However, the applicant has demonstrated that the abovementioned compounds do not make it possible to achieve a sufficient level of volatile substances impregnated into the material, nor a satisfactory diffusion profile of these substances, in particular in the case of silicone materials.

Moreover, U.S. Pat. No. 6,379,689 describes diffusers comprising a matrix based on a silicone elastomer in which are dispersed a volatile substance, such as a fragrance or an insecticide, and also an agent intended to improve the compatibility of the volatile substance with the matrix, which is chosen from ethers such as 3-methyl-3-methoxybutanol. The volatile substance and the compatibilizing agent are mixed with the liquid silicone resin which is then crosslinked. They are thus trapped in the silicone matrix during the synthesis thereof. It has been observed by the applicant that these compatibilizing agents have the same limitations as the solvents described in FR 1 601 586. Moreover, these compatibilizing agents do not make it possible to limit the phenomena of exudation of the volatile substance during storage, which must be counteracted by the addition of a surfactant to the mixture to be polymerized. Finally, the method for producing the diffusers disclosed in document U.S. Pat. No. 6,379,689 is complex, which necessarily has an impact on the cost price of said diffusers.

There thus remains the need to provide a solid polymeric material capable of diffusing a volatile organic substance in a sustained manner, which volatile organic substance can be introduced into the material in sufficient amount by simple impregnation.

It would also be useful to have an article made of solid polymeric material based on silicone resin which can be impregnated with a sufficient amount of volatile organic substance without undergoing deformation, in particular swelling.

SUMMARY OF THE INVENTION

The applicant has demonstrated that the abovementioned needs can be satisfied by impregnating a solid polymeric material with a solution containing, in addition to a volatile organic substance (such as a fragrance), a specific ester which makes it possible to improve the rate of infusion of the volatile organic substance into the material and its diffusion profile.

A subject of the invention is thus a solid polymeric material impregnated with a volatile organic substance and with a solvent comprising a $C_{10}$-$C_{18}$ monoester of a $C_1$-$C_8$ alkyl.

A subject of the invention is also a method for producing this material, characterized in that it comprises the following steps:
(a) solubilizing the volatile organic substance in the solvent, and
(b) impregnating the solid polymeric material with the solution thus obtained.

Another subject of the invention is the use of the abovementioned material for fragrancing or deodorizing the atmosphere, the body or laundry or as an insect repellant or insecticide, preferably for fragrancing the atmosphere.

Another subject of the invention is an article comprising this material, characterized in that it is chosen from a fragrancing or deodorizing product, an insect repellant or an insecticide, preferably a fragrancing product.

DETAILED DESCRIPTION

The invention relates to a solid polymeric material. The term "solid" is intended to mean that the form and dimensions of the material do not vary at ambient temperature, in the absence of force applied to the material.

This polymeric material may comprise a thermoplastic or thermosetting polymer or an elastomer, provided that the material has a sufficient gas permeability and that it is not soluble in the solvents described below. It is advantageously an elastomer. The elastomer can be obtained by crosslinking one or more organic or organomineral liquid precursors, chosen from silicone resins, fluoroelastomers, perfluoroelastomers, natural rubber, synthetic polyisoprene, polybutadiene, styrene-butadiene copolymers, polyisobutylene (PIB), chloroprene, butadiene/acrylonitrile copolymers, ethylene-propylene (EP or EPM) copolymers, ethylene/propylene/diene (EPDM) terpolymers, polyether block amides (PEBAs), block polymers of the EPDM-polypropylene type, thermoplastic polyurethanes (TPUs), thermoplastic olefins (TPOs), polysulfides, ethylene/vinyl acetate (EVA or EVM) copolymers, polyacrylic (ACM) elastomers, acrylic ethylene (AEM) copolymers, chlorosulfonated polyethylene (CSM), epichlorohydrin (CO and ECO) elastomers and mixtures thereof.

The polymeric material according to the invention preferably comprises a silicone elastomer obtained from at least one silicone resin, alone or as a mixture with at least one other polymer. The silicone elastomer is generally obtained by reacting an organopolysiloxane with either an organic peroxide, or a crosslinking agent in the presence of a catalyst. The crosslinking agent may be, in the case of a two-component resin, a polysiloxane containing at least one reactive group (hydrogen, allyl or vinyl, in particular) capable of reacting with a reactive group borne by the organopolysiloxane (which is, for example, an organohydropolysiloxane). It is clearly understood that the above-mentioned reactive groups can be located at the end position and/or the lateral position of the polysiloxane chain. The organopolysiloxane forming the liquid precursor and the crosslinking agent each have, in principle, a polydimethylsiloxane backbone of which one or more methyl groups have optionally been substituted with phenyl groups. In the case of a single-component resin, the organopolysiloxane generally comprises a silanol end and the crosslinking agent may be an alkyltrialkoxysilane such as methyltriacetoxysilane. In any event, the catalyst is generally based on tin and/or titanium.

The polymeric material may also contain one or more additives normally used in such materials, chosen from: organic and/or inorganic fillers; reinforcing agents; plasticizers; pigments and/or dyes; antioxidants; flame retardants; UV absorbers; light stabilizers; impact modifiers; antistatic agents; fungicides; and mixtures thereof.

This material may for example have a Shore A hardness ranging from 10 to 100, preferentially from 20 to 80.

In any event, those skilled in the art will know how to select the material suitable for the diffusion of the chosen volatile organic substance, in such a way that the second does not degrade the first under normal conditions of use.

The solid polymeric material is impregnated with a volatile organic substance. The term "volatile organic substance" is intended to mean a product consisting of one or more organic molecules, which has a vapor pressure greater than atmospheric pressure at ambient temperature. The volatile organic substance used according to the invention can advantageously be chosen from a fragrance, an odor-masking agent and an insecticide, preferably a fragrance.

In the context of this description, the term "fragrance" is intended to mean a single odor-emitting volatile compound or a mixture of odor-emitting volatile compounds. These compounds are in particular listed in the Merck Index, 8th Edition, Merck & Co., Inc. Rahway, N.J. These compounds may be of synthetic or natural origin. There may for example be one or more essential oils of plants, chosen for example from Asteraceae, Myrtaceae, Lauraceae, Lamiaceae, Rutaceae and Zingiberaceae, which are usually extracted from any part of these plants by extraction using a supercritical fluid, hydrodistillation, enfleurage, steam distillation or any other process which enables the extraction of fragranced molecules from a plant.

Whether they are of synthetic or natural origin, the fragrances comprise in general compounds, that are generally terpenic or aromatic, chosen from hydrocarbons, alcohols and esters thereof, aldehydes, esters, acetals and ketones, and also $C_{12}$-$C_{16}$ macrocyclic compounds, heterocyclic compounds such as pyrazines and indoles, and mixtures thereof.

The following fragrancing compounds can in particular be used as fragrance in the present invention, alone or in combination: methyl 2-methylbutyrate; isopropyl 2-methylbutyrate; ethyl 2-methylbutyrate; ethyl 2-methylpentanoate; ethyl heptanoate; ethyl octanoate; isobutyl hexanoate; amyl butyrate; amyl heptanoate; isoamyl isobutyrate; hexyl acetate; hexyl butyrate; hexyl isobutyrate; hexyl isovalerate; hexyl propionate; ethyl 2-cyclohexylpropanoate; ethyl 3,5,5-trimethylhexanoate; glyceryl 5-hydroxydecanoate; prenyl acetate; methyl 2-butenylacetate; methyl 3-nonenoate; ethyl decenoate; ethyl octenoate; ethyl decadienoate; ethyl octenoate; citronellyl acetate; 2-hex-1-enyl isovalerate; 2-hexen-1-yl propionate; 2-hexenen-1-yl valerate; (E)-3-hexen-1-yl 2-hexenoate; 3-hexen-1-yl 2-methylbutyrate; 3-hexen-1-yl acetate; 3-hexen-1-yl benzoate; 3-hexen-1-yl formate; 3-hexen-1-yl tiglate; 2-methylbutyl 2-methylbutyrate; butyl isovalerate; allylcyclohexane; allylcyclohexyl propionate; allylcyclohexyl valerate; benzyl octanoate; gamma-decalactone; gamma-dodecalactone; jasmine lactone; jasmolactone; nonalactone; 6-acetoxydihydrotheaspirane; phenoxyethyl isobutyrate; pivacyclene; dimethyl anthranilate; methyl anthranilate; octanal; nonanal; decanal; dodecanal; methyl nonyl acetaldehyde; methyl octyl acetaldehyde; 2,4-hexadienal; intreleven; decen-1-al; nonen-1-al; aldoxal; geraldehyde; isocyclocitral; d-limonene; ligustral; tridecenal; triplal; vertoliff; cyclal C; heliotropin; neocaspirene; beta-naphthol ethyl ether; beta-naphthol methyl ether; hyacinth ether; 2-heptyl cyclopentanone; undecavertol; frutonile; and mixtures thereof.

As a variant, the volatile organic substance according to the invention may constitute an odor-masking agent. Such agents may in particular be chosen from: saturated, optionally alkoxylated, aldehydes, such as 2-methylundecanal and 6-methoxy-2,6-dimethyloctanal; unsaturated aldehydes, such as 2,6-dimethylhept-5-enal, 2,4-dimethylcyclohex-3-enecarbaldehyde, 4-vinylcyclohex-1-enecarbaldehyde and bicyclo[2.2.2]oct-5-ene-2-carboxaldehyde; aromatic aldehydes, such as 4-methylbenzaldehyde; glycolates, such as allyl-2-(isopentyloxy)acetate; alcohols, such as linalool, nona-2,6-dien-1-ol, non-6-en-1-ol, 2,6-dimethylheptan-2-ol and cis-hex-3-en-1-ol; sulfur-comprising fragrances, such as 2-(4-methylcyclohex-3-en-1-yl)propane-2-thiol and 4,7,7-trimethyl-6-thiabicyclo[3.2.1]octane; benzodioxepines, such as 7-methyl-2H-benzo[b][1,4]dioxepin-3-4H)-one; ketones, such as 3-methyl-2-pentylcyclopent-2-enone and 2-methyl-5-(prop-1-en-2-yl)cyclohex-2-enone; furans, such as 5-tert-butyl-2-methyl-5-propyl-2H-furan; pyrans, such as 4-methylene-2-phenyltetrahydro-2H-pyran; phenols, such as eugenol (4-allyl-2-methoxyphenol); phenolic esters, such as p-tolyl acetate; nitriles, such as 4-isopropylbenzonitrile; aromatic ethers, such as 1-methoxy-4-propylbenzene; esters, such as ethyl isobutyrate, hexenyl acetate and ethyl isovalerate; lactones, such as 5-pentyldihydrofuran-2(3H)-one; anthranilates, such as methyl 2-aminobenzoate; carboxylic acids, such as 2-phenylacetic acid; terpenes, such as 7-methyl-3-methyleneocta-1,6-diène; and mixtures thereof.

Another example of an odor-masking agent consists of a combination of 1,8-para-menthenethiol and 3-mercaptohexyl acetate or of an essential oil of Timur (*Zanthoxylum armatum*) containing this combination, which can be obtained from any part of the Timur and in particular from its leaves, from its trunk, from its fruits (berries) or from their pericarp, more preferentially from its berries.

As a further variant, the volatile organic substance according to the invention may constitute an insecticide. Examples of insecticides include in particular: essential oils such as those of patchouli, peppermint, cypress, pine, Perilla, pyrethrum (*Tanacetum cinerariifolium*), catnip, lavender, coriander, eucalyptus, citronella, lime, neroli, rosemary, hyssop, rose, ylang-ylang, pepper, cinnamon, camphor, chamomile, bay, tarragon, absinthe, clover, geranium, sage, basil, parsley, star anise, fennel, galbanum, manuka, violet, dill, angelica, turmeric, ginger, ambrette and gaultheria; synthetic compounds such as N,N'-diethyl-3-methylbenzamide (DEET), p-menthane-3,8-diol, 2-undecanone, 1-piperidinecarboxylic acid 2-(2-hydroxyethyl)-1-methyl propyl ester and ethyl butylacetylaminopropionate (IR 3535); and mixtures thereof.

The volatile organic substance is solubilized in a particular solvent before being introduced into the solid polymeric material described above. In any event, those skilled in the art will know how to choose a volatile organic substance that is soluble in sufficient amount for the desired application in the solvent described below.

This solvent comprises a $C_{10}$-$C_{18}$ monoester of a $C_1$-$C_8$ alkyl, such as methyl laurate, isopropyl laurate, ethylhexyl laurate, isopropyl myristate, butyl stearate, isobutyl stearate, ethyl palmitate or ethylhexyl palmitate, without this list being limiting. A $C_{12}$-$C_{16}$ monoester of a $C_3$-$C_6$ alkyl is preferably used, more preferentially isopropyl myristate.

In the case where the solid polymeric material comprises a silicone elastomer, it is preferable for the solvent to also contain a saturated $C_2$-$C_{10}$ diester of a $C_3$-$C_{12}$ alkyl, such as dimethyl succinate, diethyl succinate, diethylhexyl succinate, dimethyl glutarate, dimethyl adipate, diisopropyl adipate, diisobutyl adipate, octyl adipate, dimethyl sebacate, diethyl sebacate, diisopropyl sebacate, dibutyl sebacate or dioctyl sebacate, without this list being limiting. A saturated $C_4$-$C_8$ diester of a $C_6$-$C_{10}$ alkyl, more preferentially dioctyl adipate, is preferably used. It has in fact been demonstrated that the combination of this diester with the abovementioned monoester makes it possible to prevent swelling of certain silicone materials without being detrimental to the other desired properties for these materials. The mass ratio of the $C_{10}$-$C_{18}$ monoester of a $C_1$-$C_8$ alkyl to the saturated $C_2$-$C_{10}$ diester of a $C_3$-$C_{12}$ alkyl may in particular be between 5:95 and 95:5, preferably between 40:60 and 60:40.

Advantageously, the $C_{10}$-$C_{18}$ monoester of a $C_1$-$C_8$ alkyl and the saturated $C_2$-$C_{10}$ diester of a $C_3$-$C_{12}$ alkyl, when it is present, represent at least 50% by weight, preferably at least 70% by weight, more preferentially at least 90% by weight, better still at least 95% by weight, relative to the weight of the solvent according to the invention. Better still, the solvent used according to the invention does not contain any compound other than the $C_{10}$-$C_{18}$ monoester of a $C_1$-$C_8$ alkyl and the saturated $C_2$-$C_{10}$ diester of a $C_3$-$C_{12}$ alkyl, when it is present.

The concentration of the volatile organic substance in the solvent may be between 20 and 95% by weight, preferably between 30 and 90% by weight and more preferentially between 50 and 80% by weight.

The material described above can be prepared according to a process comprising the impregnation of the solid polymeric material with a solution comprising the volatile organic substance in the solvent.

In one preferred embodiment of the invention, the volatile organic substance and the solvent described above represent at least 50%, more preferentially at least 70%, better still at least 90%, even better still at least 95% of the weight of the solution. More particularly, the solution consists only of the solvent and the volatile organic substance. As a variant, the infusion solution can comprise one or more additives chosen from antioxidants, antifungals, dyes, light stabilizers, UV absorbers, viscosity agents, surfactants and mixtures thereof.

This solution can be prepared by simply mixing its constituents at ambient temperature, generally with stirring.

The impregnation of the solid polymeric material with this solution can be carried out by any means known to those skilled in the art and in particular by dipping or spraying, preferentially by dipping the material in a bath consisting of the solution. An advantage of the present invention is that one and the same bath can be used several times, typically two or three times, but possibly until the solution has been totally consumed, and thus makes it possible to prepare several articles from a single solution. The impregnation step is usually carried out at ambient temperature, but is also possible at any temperatures for which the solution is in the liquid state, thus making it possible to accelerate or slow down the total or partial infusion of the solution in the material.

The impregnated material thus obtained can be used for fragrancing or deodorizing the atmosphere, the body or laundry or as an insect repellant or insecticide, preferably for fragrancing the atmosphere. When it is used as a fragrancing or deodorizing product, this material can be used in any type of environment, in particular in premises for domestic, commercial or industrial use or in a car. As a variant, it can be introduced into the drum of a washing machine or a tumble dryer, or can be used as a component of a fashion accessory (in particular a handbag, a jewel or a watch).

The invention therefore also relates to an article comprising the material described above, chosen from a fragrancing or deodorizing product, an insect repellant or an insecticide, preferably a fragrancing product. This article can be provided in any shape suitable for these uses and in particular can be provided in the form of a ring, a pebble stone, a ball, a cube, a cylinder, a dome or a pyramid suitable for being placed, suspended or carried. To do this, it is sufficient for the material to be molded in the desired shape before impregnation with the volatile organic substance. It will be noted that it is possible to increase the amount of volatile substance incorporated into the article, either by increasing its size (with constant shape), or by varying its shape so as to increase its surface area, and thus to vary the duration of use of the article as a function of the envisioned application.

FIGURES

EXAMPLES

The invention will be understood more clearly in light of the following examples, which are given purely by way of illustration and are not intended to limit the scope of the invention, defined by the appended claims.

Example 1: Influence of the Solvent on the Rate of Infusion

The rate of infusion in a silicone material of a fragrance carried in various solvents was measured. To do this, identical silicone elastomer rings were each weighed and then immersed for various periods of time (1 h, 4 h, 18 h and 24 h) in a solution containing the same fragrance in a different solvent, namely: ethanol (EtOH), methyl oleate, isopropylideneglycerol (Augeo MC), isopropyl myristate (IPM), 3-methyl-3-methoxybutanol (MMB), dioctyl adipate (DOA) and a 50:50 (w/w) mixture of isopropyl myristate and dioctyl adipate (DOA/IPM). The fragrance concentration in the solution ranged from 50% by weight (for the individual solvents) to 80% by weight (for the mixture of solvents). The ring was removed at the end of the time period in question and weighed to determine the percentage of fragrance that it contained.

Figure 1:
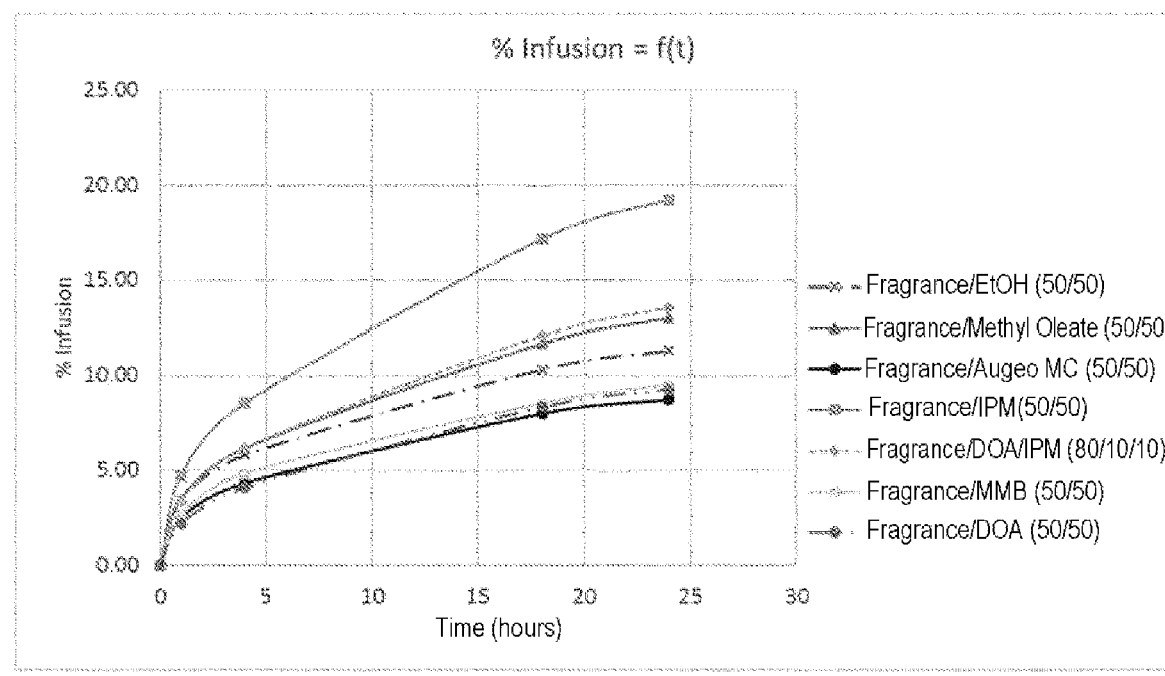
FIG. 1 illustrates the variation, as a function of time, of the rate of infusion of a fragrance in a polymeric material impregnated with a solution of this fragrance in various solvents.

The results of these tests are illustrated in FIG. 1. As shown in this figure, isopropyl myristate makes it possible to obtain the highest rate of infusion. The rate of infusion decreases when this solvent is mixed with dioctyl adipate, nevertheless remaining higher than the levels that it was possible to obtain with other solvents such as 3-methyl-3-methoxybutanol, used as a compatibilizing agent in U.S. Pat. No. 6,379,689, and the alkyl diesters as described in FR 1 601 586.

Example 2: Influence of the Solvent on the Rate of Release

The rate of release or of diffusion of a fragrance carried in various solvents and infused in the same silicone material was measured. To do this, identical silicone elastomer rings were each immersed for 24 h in a solution containing the same fragrance in a different solvent, namely: ethanol (EtOH), methyl oleate, isopropylideneglycerol (Augeo MC), isopropyl myristate (IPM), 3-methyl-3-methoxybutanol (MMB), dioctyl adipate (DOA) and a 50:50 (w/w) mixture of isopropyl myristate and dioctyl adipate (DOA/IPM). The fragrance concentration in the solution ranged from 50% by weight (for the individual solvents) to 80% by weight (for the mixture of solvents). The ring was then weighed after various storage times at ambient temperature in order to determine the percentage of fragrance remaining in the ring.

Figure 2:
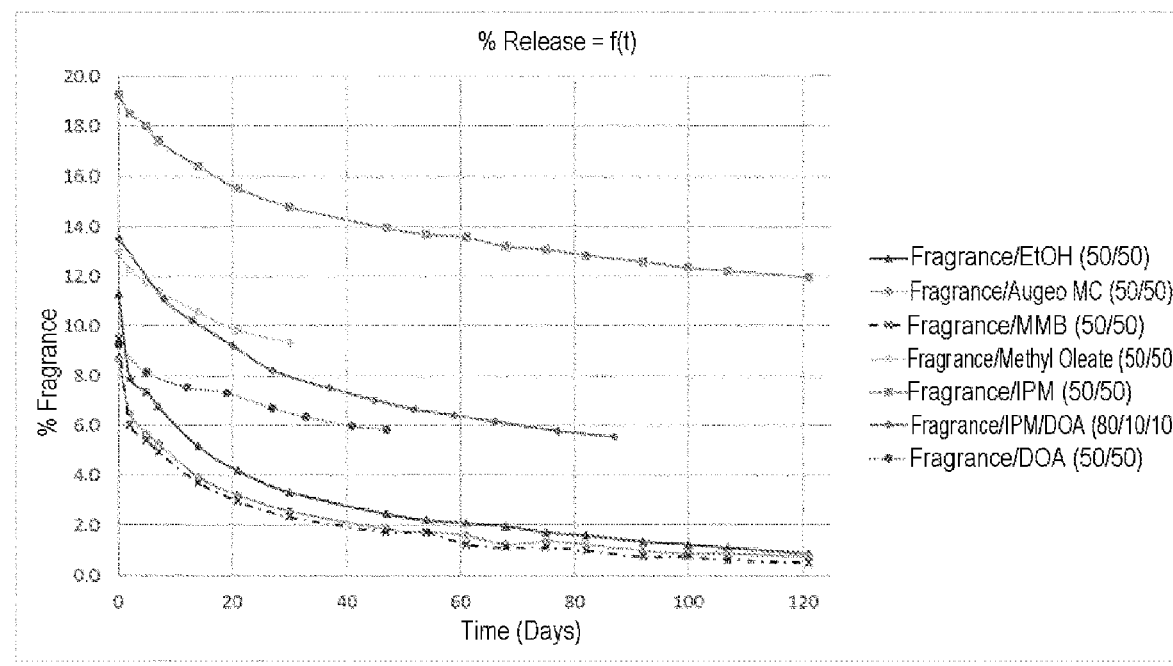
FIG. 2 illustrates the variation, as a function of time, of the rate of release of a fragrance infused in a polymeric material by means of a solution containing various solvents.

The results of these tests are illustrated in FIG. 2. As shown in this figure, the fragrance release kinetics depend on the solvent tested. Isopropyl myristate allows a gradual diffusion of the fragrance which remains present in the ring in a much higher amount, after 120 days, than those which can be obtained with the other solvents tested, in particular 3-methyl-3-methoxybutanol and dioctyl adipate. It will be noted that the test using methyl oleate was interrupted because of exudation of the solvent.

Additional tests made it possible to show that the release kinetics of the fragrance carried in isopropyl myristate did not significantly vary when the concentration of the fragrance in the solvent varied from 30 to 90% by weight.

Example 3: Influence of the Solvent on the Sensory Intensity of the Fragrance

The sensory intensity of a fragrance carried in various solvents and infused in the same silicone material was measured. To do this, identical silicone elastomer rings were each immersed for 24 h in a solution containing the same fragrance in a different solvent, namely: ethanol (EtOH), methyl oleate, isopropylideneglycerol (Augeo MC), isopropyl myristate (IPM), 3-methyl-3-methoxybutanol (MMB), dioctyl adipate (DOA) and a 50:50 (w/w) mixture of isopropyl myristate and dioctyl adipate (DOA/IPM). The fragrance concentration in the solution ranged from 50% by weight (for the individual solvents) to 80% by weight (for the mixture of solvents). The ring was then stored at ambient temperature in a cupboard for two months. A panel of trained experts evaluated the sensory intensity of the fragrance after various storage times. Said intensity was scored on a scale of 0 to 10 where 10 corresponds to the initial sensory intensity of the fragrance.

Figure 3:
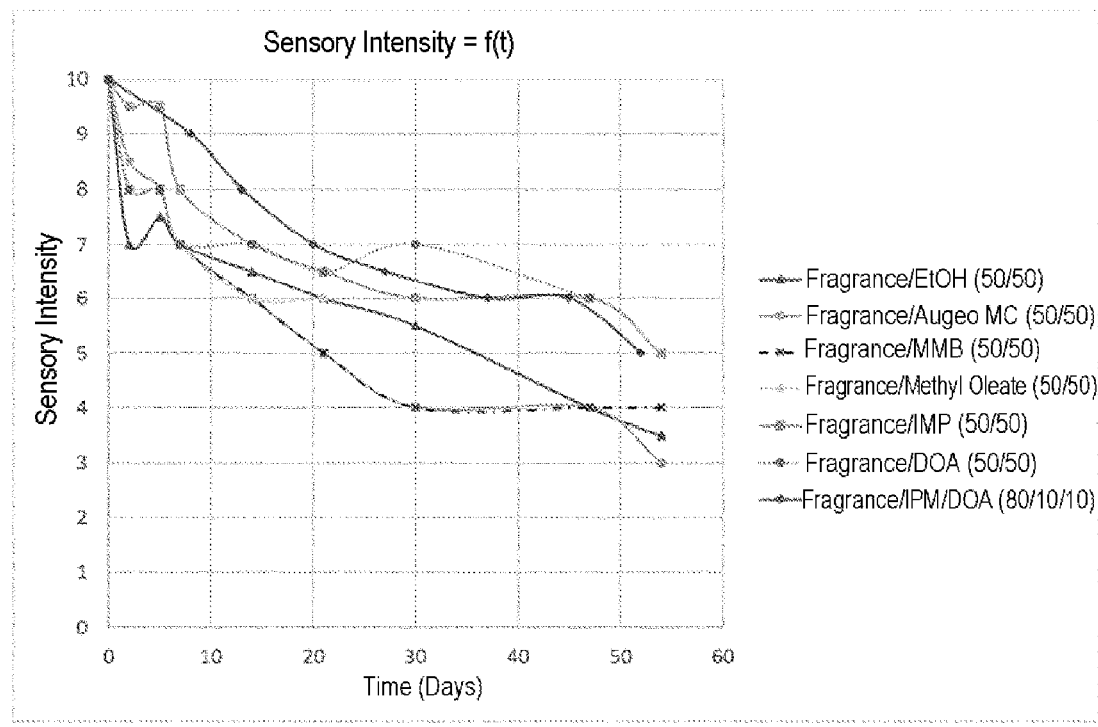
FIG. 3 represents the variation, as a function of time, of the sensory intensity given off by a fragrance infused in a polymeric material by means of a solution containing various solvents.

The results of these tests are illustrated in FIG. 3. As shown in this figure, the sensory intensity of the fragrance in solution in isopropyl myristate, alone or as a mixture with dioctyl adipate, drops less strongly than in the presence of the other solvents (in particular 3-methyl-3-methoxybutanol) and decreases in a more linear manner than with dioctyl adipate alone.

Example 4: Influence of the Solvent on the Swelling of the Material

Figure 4:
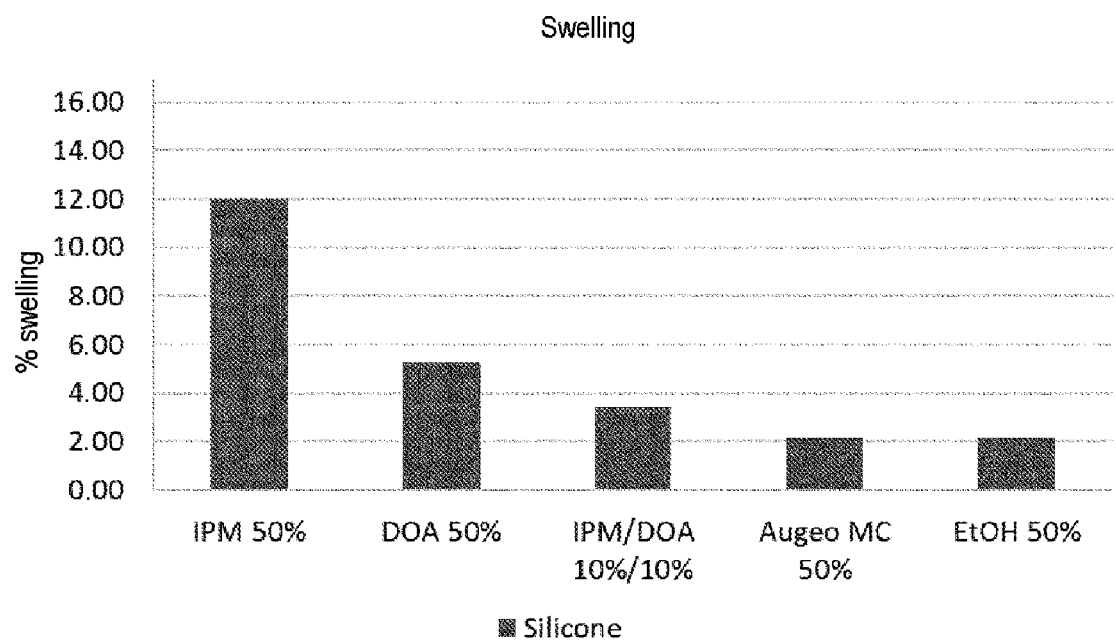
FIG. 4 represents the degree of swelling of a silicone material impregnated with a solution containing a fragrance in various solvents.

The degree of swelling of a silicone elastomer ring in various solvents was measured, said solvents being namely: ethanol (EtOH), isopropylideneglycerol (Augeo MC), isopropyl myristate (IPM), dioctyl adipate (DOA) and a 50:50 (w/w) mixture of isopropyl myristate and dioctyl adipate (DOA/IPM). The fragrance concentration in the solution ranged from 50% by weight (for the individual solvents) to 80% by weight (for the mixture of solvents). It was observed, as emerges from FIG. 4, that the swelling of the material was greatest in isopropyl myristate and that it could be significantly reduced by combining it with dioctyl adipate. As demonstrated in examples 1 to 3, the IPM/DOA mixture makes it possible to incorporate a considerable amount of fragrance into the material and has good fragrance diffusion properties, such that it constitutes a choice solvent for silicone-elastomer-based materials.

Example 5: Influence of the Hardness of the Material

The rate of infusion of a fragrance carried in isopropyl myristate (20% w/w) in various silicone elastomers, prepared from silicone resins having a Shore A hardness ranging from 30 (MED-4930 from NuSil) to 80 (MED-4980 from NuSil), was evaluated in a manner similar to example 1.

Figure 5:
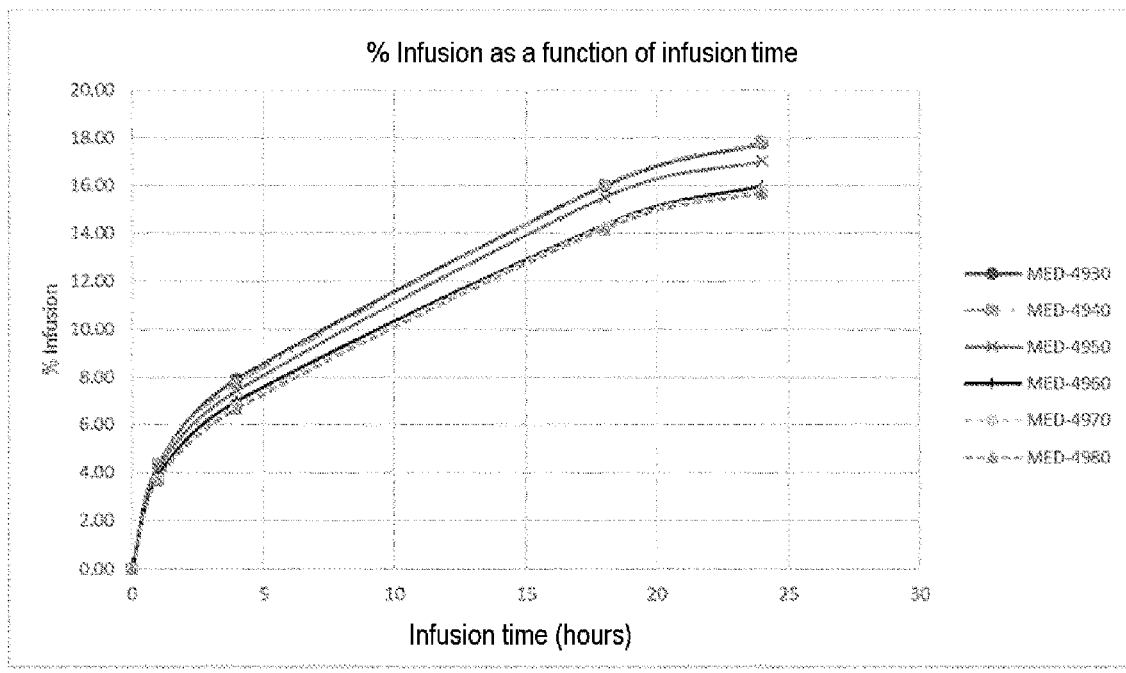
FIG. 5 illustrates the variation, as a function of time, of the rate of infusion of a fragrance in silicone materials with various hardnesses.

The results of this test are presented in FIG. 5. As shown in this figure, the hardness of the elastomer has little impact on the rate of infusion of the fragrance, the hardest materials being slightly less charged with fragrance than the softer materials.

Figure 6:
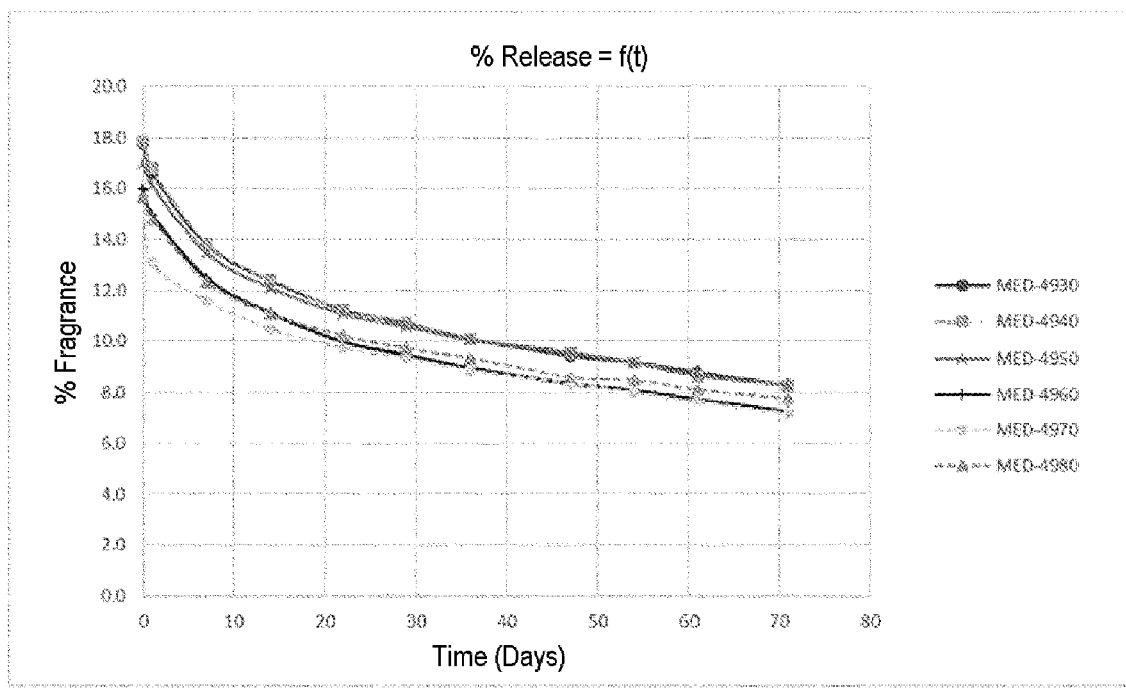
FIG. 6 illustrates the variation, as a function of time, of the rate of release of a fragrance infused in silicone materials of various hardnesses.

The rate of release of the fragrance by these various materials was also measured in a manner similar to example 2. As illustrated in FIG. 6, the hardness of the elastomer has a non-significant impact on the release properties of the fragrance, insofar as the slope of the curve obtained as a function of time varies little.

The invention claimed is:

1. A solid polymeric material impregnated with a volatile organic substance and with a solvent comprising isopropyl myristate, wherein the solid polymeric material is prepared by a process comprising the following steps:
(a) solubilizing the volatile organic substance in the solvent comprising isopropyl myristate to form a solution, and
(b) impregnating the solid polymeric material with the solution obtained from step (a), wherein the solid polymeric material comprises a thermoplastic polymer or an elastomer.

2. The material according to claim 1, wherein the volatile organic substance is selected from the group consisting of: a fragrance, an odor-masking agent and an insecticide.

3. The material according to claim 2, wherein the volatile organic substance is a fragrance.

4. The material according to claim 1, wherein the concentration of the volatile organic substance in the solvent is between 20 and 95% by weight.

5. The material according to claim 4, wherein the concentration of the volatile organic substance in the solvent is between 30 and 90% by weight.

6. The material according to claim 4, wherein the concentration of the volatile organic substance in the solvent is between 50 and 80% by weight.

7. The material according to claim 1, which comprises a silicone elastomer.

8. The material according to claim 7, wherein the solvent also contains a saturated $C_2$-$C_{10}$ diester of a $C_3$-$C_{12}$ alkyl.

9. The material according to claim 8, wherein the saturated $C_2$-$C_{10}$ diester of a $C_3$-$C_{12}$ alkyl is a saturated $C_4$-$C_8$ diester of a $C_6$-$C_{10}$ alkyl.

10. The material according to claim 9, wherein the mass ratio of isopropyl myristate to the saturated $C_2$-$C_{10}$ diester of a $C_3$-$C_{12}$ alkyl is between 40:60 and 60:40.

11. The material according to claim 8, wherein the saturated $C_2$-$C_{10}$ diester of a $C_3$-$C_{12}$ alkyl is dioctyl adipate.

12. The material according to claim 8, wherein the mass ratio of isopropyl myristate to the saturated $C_2$-$C_{10}$ diester of a $C_3$-$C_{12}$ alkyl is between 5:95 and 95:5.

13. A method for fragrancing or deodorizing the atmosphere, comprising contacting the atmosphere with the material according to claim 1.

14. A method for fragrancing or deodorizing laundry, comprising introducing the material according to claim 1 into the drum of a washing machine or a tumble dryer.

15. An article comprising the material according to claim 1, which is selected from the group consisting of: a fragrancing or deodorizing product, an insect repellant and an insecticide.

16. The article according to claim 15, wherein the article is a fragrancing product.

* * * * *